(12) United States Patent
Puzella et al.

(10) Patent No.: US 11,986,566 B2
(45) Date of Patent: May 21, 2024

(54) SYSTEM AND METHOD FOR DECONTAMINATION OF MATERIALS

(71) Applicant: Raytheon Company, Waltham, MA (US)

(72) Inventors: Angelo M. Puzella, Marlboro, MA (US); Joseph T. Mossoba, Wellesley, MA (US); Sharon A. Elsworth, Mason, NH (US); John Sangiolo, Auburndale, MA (US)

(73) Assignee: Raytheon Company, Tewksbury, MA (US)

( * ) Notice: Subject to any disclaimer, the term of this patent is extended or adjusted under 35 U.S.C. 154(b) by 793 days.

(21) Appl. No.: 17/086,900

(22) Filed: Nov. 2, 2020

(65) Prior Publication Data

US 2022/0133927 A1 May 5, 2022

(51) Int. Cl.
*A61L 2/12* (2006.01)
*H01P 1/38* (2006.01)
*H01Q 13/02* (2006.01)
*H03F 3/24* (2006.01)

(52) U.S. Cl.
CPC .................. *A61L 2/12* (2013.01); *H01P 1/38* (2013.01); *H01Q 13/02* (2013.01); *H03F 3/245* (2013.01); *A61L 2202/15* (2013.01); *H03F 2200/451* (2013.01)

(58) Field of Classification Search
CPC .......... H05B 6/72; H03F 3/245; H01Q 13/02; H01P 1/38; A61L 2/08; A61L 2/12
See application file for complete search history.

(56) References Cited

U.S. PATENT DOCUMENTS

| | | | |
|---|---|---|---|
| 5,106,594 A | | 4/1992 | Held et al. |
| 5,523,052 A | * | 6/1996 | Bridges ..................... A61L 2/08 |
| | | | 422/26 |
| 5,543,111 A | | 8/1996 | Bridges et al. |
| 5,980,824 A | | 11/1999 | Kartchner |
| 2003/0194692 A1 | | 10/2003 | Purdum |

(Continued)

FOREIGN PATENT DOCUMENTS

| | | | | |
|---|---|---|---|---|
| EP | 3566722 A1 | * | 11/2019 | ............... A61L 2/12 |
| WO | WO-9964075 A1 | * | 12/1999 | ............. A01B 79/00 |

OTHER PUBLICATIONS

International Search Report and Written Opinion of the International Searching Authority dated Feb. 28, 2022 in connection with International Patent Application No. PCT/US2021/056463, 10 pages.

*Primary Examiner* — Sean E Conley
*Assistant Examiner* — Justin Hwang

(57) ABSTRACT

A system includes a container configured to hold one or more items contaminated with a contaminant. The system also includes a power amplifier configured to output radio frequency (RF) energy at a frequency substantially equal to a resonant frequency of the contaminant. The system further includes a horn connected to the power amplifier and configured to propagate the RF energy along a length of the container and through the one or more items to deactivate, damage, or destroy the contaminant by molecular resonance. In addition, the system includes an RF absorbing liner disposed on interior surfaces of the container and configured to absorb and reduce reflection of at least some of the RF energy.

20 Claims, 6 Drawing Sheets

(56) References Cited

U.S. PATENT DOCUMENTS

| | | |
|---|---|---|
| 2006/0024195 A1 | 2/2006 | Lagunas-Solar et al. |
| 2017/0232122 A1 | 8/2017 | Hancock |
| 2019/0209725 A1 | 7/2019 | Henniges et al. |
| 2019/0314537 A1 | 10/2019 | Norling |
| 2020/0046865 A1 | 2/2020 | Shane et al. |
| 2020/0205446 A1 | 7/2020 | Ching et al. |
| 2020/0237939 A1 | 7/2020 | Henniges et al. |
| 2020/0267876 A1 | 8/2020 | Nguyen |

\* cited by examiner

SYSTEM AND METHOD FOR DECONTAMINATION OF MATERIALS

TECHNICAL FIELD

This disclosure is directed in general to decontamination techniques. More specifically, this disclosure relates to a system and method for decontamination of materials.

BACKGROUND

Due to the onset of the COVID-19 (CV-19) pandemic, there is an urgent need to safely and efficiently disinfect or otherwise decontaminate personal protective equipment (PPE), such as surgical masks, gowns, and booties. The need is especially great for healthcare and nursing home professionals and for workers in restaurant and hospitality businesses. Presently, some decontamination techniques use vaporized hydrogen peroxide released inside a container containing contaminated items in order to decontaminate the items. However, these techniques suffer from a number of drawbacks.

SUMMARY

This disclosure provides a system and method for decontamination of materials, such as personal protective equipment (PPE).

In a first embodiment, a system includes a container configured to hold one or more items contaminated with a contaminant. The system also includes a power amplifier configured to output radio frequency (RF) energy at a frequency substantially equal to a resonant frequency of the contaminant. The system further includes a horn connected to the power amplifier and configured to propagate the RF energy along a length of the container and through the one or more items to deactivate, damage, or destroy the contaminant by molecular resonance. In addition, the system includes an RF absorbing liner disposed on interior surfaces of the container and configured to absorb and reduce reflection of at least some of the RF energy.

In a second embodiment, a system includes a container configured to hold one or more items contaminated with a contaminant. The system also includes first and second power amplifiers, where each power amplifier is configured to output RF energy at a frequency substantially equal to a resonant frequency of the contaminant. The system further includes first and second horns, where each horn is connected to one of the power amplifiers and is configured to propagate the RF energy from that power amplifier along a length of the container and through the one or more items to deactivate, damage, or destroy the contaminant by molecular resonance. In addition, the system includes an RF absorbing liner disposed on interior surfaces of the container and configured to absorb and reduce reflection of at least some of the RF energy.

In a third embodiment, a method includes receiving one or more items in a container, where the one or more items are contaminated with a contaminant. The method also includes outputting RF energy by at least one power amplifier at a frequency substantially equal to a resonant frequency of the contaminant. The method further includes propagating the RF energy along a length of the container and through the one or more items to deactivate, damage, or destroy the contaminant by molecular resonance using at least one horn, where each of the at least one horn is connected to one of the at least one power amplifier. In addition, the method includes absorbing and reducing reflection of at least some of the RF energy using an RF absorbing liner disposed on interior surfaces of the container.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

Figure 1:
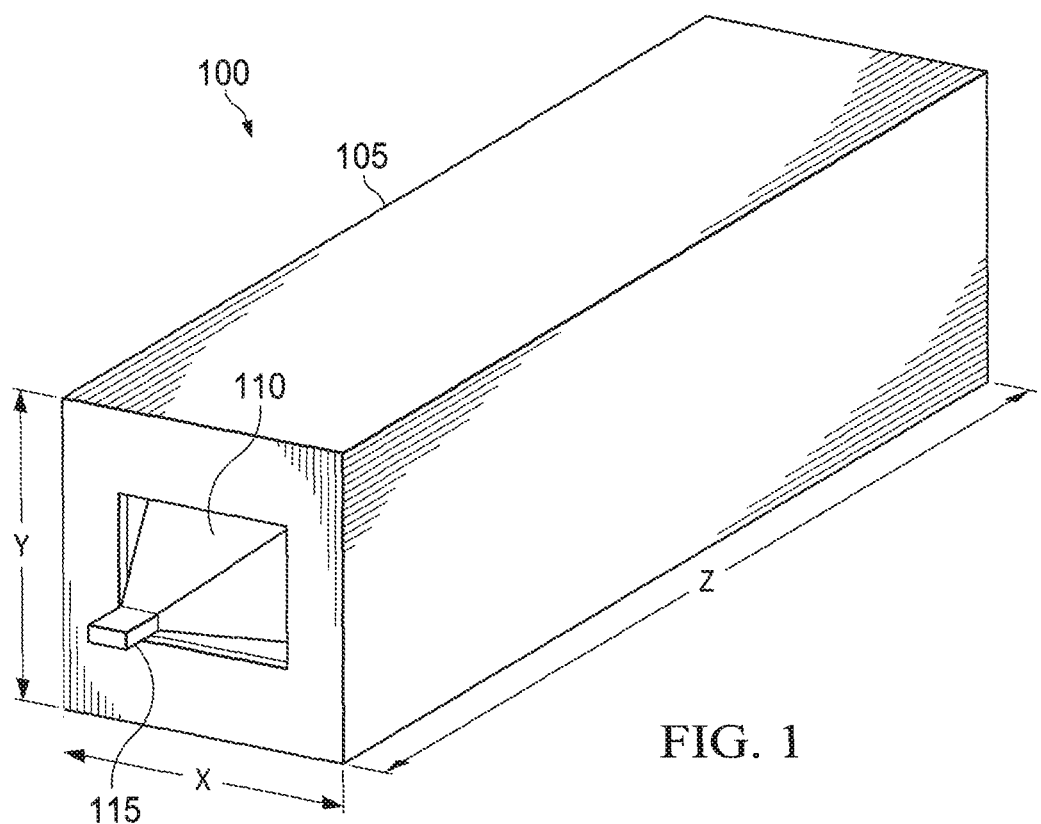
FIGS. 1 through 4 illustrate an example decontamination system according to this disclosure.

FIGS. 1 through 10, described below, and the various embodiments used to describe the principles of the present disclosure in this patent document are by way of illustration only and should not be construed in any way to limit the scope of the disclosure. Those skilled in the art will understand that the principles of the present disclosure may be implemented in any type of suitably arranged device or system.

For simplicity and clarity, some features and components are not explicitly shown in every figure, including those illustrated in connection with other figures. It will be understood that all features illustrated in the figures may be employed in any of the embodiments described. Omission of a feature or component from a particular figure is for purposes of simplicity and clarity and is not meant to imply that the feature or component cannot be employed in the embodiments described in connection with that figure. It will be understood that embodiments of this disclosure may include any one, more than one, or all of the features described here. Also, embodiments of this disclosure may additionally or alternatively include other features not listed here.

As discussed above, due to the onset of the COVID-19 (CV-19) pandemic, there is an urgent need to safely and efficiently disinfect or otherwise decontaminate personal protective equipment (PPE), such as surgical masks, gowns, and booties. The need is especially great for healthcare and nursing home professionals and for workers in restaurant and hospitality businesses. Presently, some decontamination techniques use vaporized hydrogen peroxide released inside a container containing contaminated items in order to decontaminate the items. However, these techniques suffer from a number of drawbacks. One drawback is associated with a slow disinfecting cycle, since the process can take one hour or more per batch. Another drawback is associated with supply chain issues, since cartridges of the hydrogen peroxide must be replenished at regular intervals, which limits widespread usage in businesses that cannot afford the time and expense of replenishing hydrogen peroxide. Yet another drawback is associated with a less than 100% effectiveness, since the penetration and virus-killing effectiveness of hydrogen peroxide inside the layers of an N95 mask or other PPE is uncertain. Still another drawback is associated with non-portability and difficulty in setup for use, since the hydrogen peroxide chambers are relatively large and heavy and are not amenable to table-top usage.

This disclosure provides decontamination systems and processes that produce substantially uniform radio frequency (RF) power densities of sufficient magnitudes at optimal frequencies in order to effectively and efficiently deactivate, damage, or destroy one or more contaminants in or on contaminated items. For example, the disclosed embodiments can be used to deactivate, damage, or destroy the CV-19 virus on or in contaminated PPE, such as surgical masks, gowns, or booties. The disclosed embodiments feature decontamination containers that are easy to use, safe, effective, and portable for table-top use. In some embodiments, the disclosed systems and methods can be used for a number of commercial applications, such as in hospitals, urgent-care facilities, nursing homes, restaurants and bars, hotels, spas and sports clubs, schools, and universities. Also, in some embodiments, the disclosed systems and methods can be used in various military applications, such as in training and operating bases, military ships, and long-range aircraft. While not specifically listed here, any other suitable applications are within the scope of this disclosure.

Figure 2:
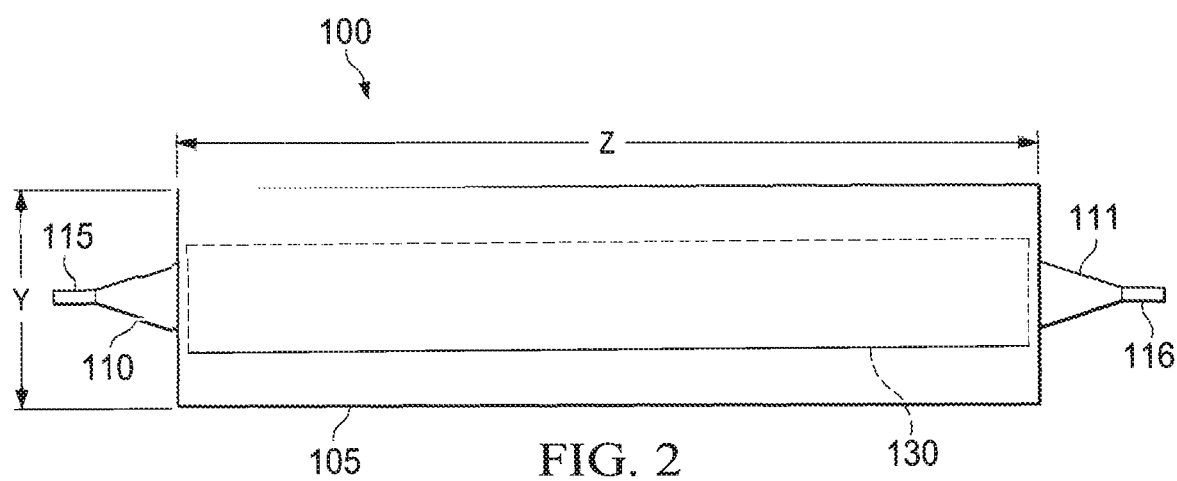
Figure 3:
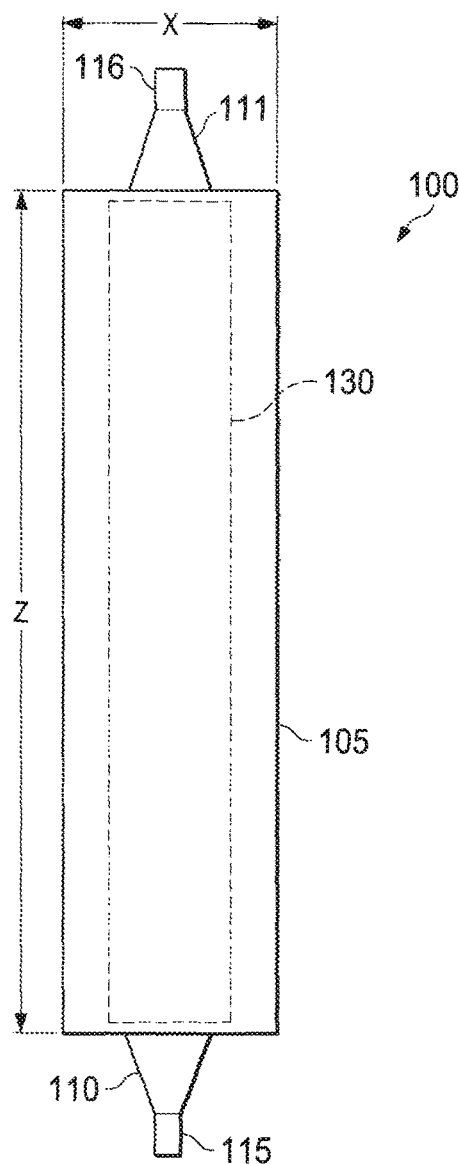
Figure 4:
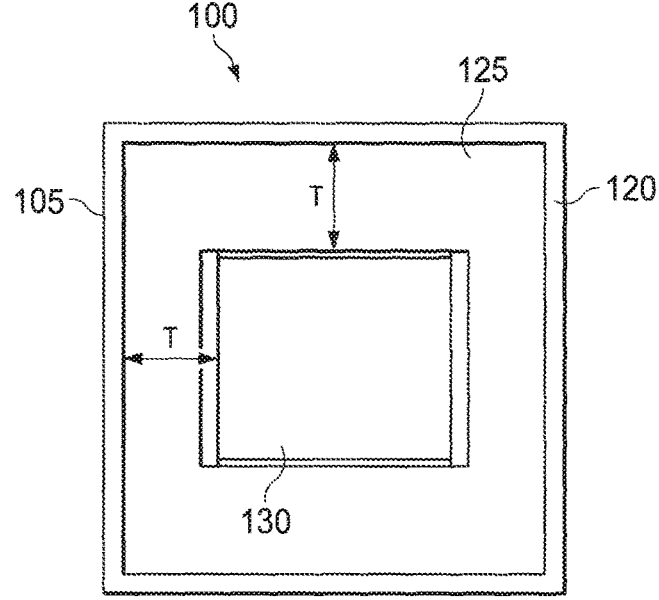

FIGS. 1 through 4 illustrate an example decontamination system 100 according to this disclosure. In particular, FIG. 1 shows an isometric view of the decontamination system 100, FIG. 2 shows a side view of the decontamination system 100, FIG. 3 illustrates a top view of the decontamination system 100, and FIG. 4 illustrates a cross-sectional view of the decontamination system 100. To promote understanding of the figures, the axes of the views are labeled X, Y, and Z.

The decontamination system 100 deactivates, damages, or destroys contaminants at room temperature using molecular resonance instead of high temperature deactivation. Some conventional systems use microwaves or other RF energy at frequencies substantially different from the resonant frequencies of contaminants. These systems merely heat up the contaminants to destroy the contaminants. In contrast, the decontamination system 100 does not significantly heat up a contaminant or a contaminated item. Instead, the decontamination system 100 uses RF energy of relatively low power density at a frequency substantially equal to the resonant frequency of a contaminant to "mechanically fracture" the contaminant. As used herein, the RF frequency is "substantially equal" to the resonant frequency of the contaminant when the RF energy can deactivate, damage, or destroy the contaminant through molecular resonance. Because a contaminated item is made of different material(s) than a contaminant, the RF energy simply passes through the contaminated item.

As shown in FIG. 1 through 4, the decontamination system 100 includes a container 105 that has an internal cavity 130. As described in greater detail below, one or more items to be decontaminated (such as PPE like surgical masks, gowns, booties, and the like) are placed in the cavity 130 within the container 105, the decontamination process is performed, and the one or more decontaminated items are removed from the container 105. In some embodiments, the container 105 has a generally rectangular shape both in profile and in cross section. However, this is merely one example, and the container 105 may have any other suitable shape, such as a cylindrical shape with a round cross section. In one particular embodiment, the container 105 is about 8 inches (about 20.3 centimeters) high by about 8 inches (about 20.3 centimeters) wide by about 30 inches (about 76.2 centimeters) long. However, this is merely one example, and other dimensions can be selected to increase or optimize RF power flow over a frequency band of interest. Although not explicitly shown in the figures, the container 105 can include one or more lids, doors, or other closeable openings to provide access to the internal cavity 130 for inserting and retrieving items to be decontaminated.

Horns 110 and 111 are disposed at opposite ends of the container 105. Each horn 110 and 111 has a wider opening that aligns with an opening of the container 105 and a narrower opening that is disposed away from the container 105. In some embodiments, each horn 110 and 111 has a rectangular cross section such as is shown in FIG. 1. In other embodiments, one or both horns 110 and 111 may have a round cross section or any other suitable shape.

Each horn 110 and 111 is connected to a corresponding power amplifier (PA) 115 and 116 that is located at or otherwise coupled to the narrower opening of the horn 110 and 111. In operation, one or both power amplifiers 115 and 116 output RF energy at a desired power density within the container 105 to decontaminate the one or more items in the container 105. In some embodiments, the power amplifiers 115 and 116 output continuous wave (CW) RF energy, which may reduce or eliminate the need for energy storage capacitors for pulsed operation. The horns 110 and 111 can be match terminated and can protect the power amplifiers 115 and 116 from high voltages. Each horn 110 and 111 can also reduce reflections inside the container 105. For example, each of the horns 110 and 111 can employ a circulator with a matched load termination, which reduces reflections inside the container 105. Due to the horns 110 and 111 disposed at the ends of the container 105, the container 105 can function as a two-port RF waveguide approximating a "free-space anechoic chamber" environment with low-level RF reflections and continuous power flow. In some embodiments, one or both of the horns 110 and 111 could include two separate ports, e.g., with different polarizations. The horns 110 and 111 could transmit RF energy from each port to achieve higher RF energy fields in the container 105.

When both power amplifiers 115 and 116 are operating, the dual-horn design enables twice the RF energy throughput for decontaminating one or more items in the container 105. In some embodiments, each of the power amplifiers 115 and 116 may operate at a power of approximately 25 watts, although other values are possible as discussed in greater detail below. Power for the power amplifiers 115 and 116 (and for any other power-consuming components of the decontamination system 100) can be received from a power supply, such as a standard electrical utility wall outlet. In some embodiments, an alternating current-to-direct current (AC/DC) power converter, such as one similar to a computer laptop "brick" power converter or other power converter, can be disposed between the power supply and the decontamination system 100.

As shown in FIG. 4, the container 105 includes an outer layer 120 that is internally lined with an RF absorbing liner 125. The outer layer 120 is a structural layer that defines the overall shape and size of the container 105. The outer layer 120 can be formed of any suitably rigid material(s). In some embodiments, the outer layer 120 is formed of one or more metals or metal alloys, such as aluminum, which reduces RF energy leakage outside of the container 105 from an amount of RF energy leakage that would occur if the outer layer 120 were not formed of one or more metals or metal alloys.

The RF absorbing liner 125 is disposed on interior surfaces of the container 105. The RF absorbing liner 125 absorbs RF energy that is output by the power amplifiers 115 and 116 as the RF energy propagates along the length of the container 105. The absorption of the RF energy by the RF absorbing liner 125 minimizes reflections of the RF energy within the container 105. In addition, the RF absorbing liner 125 reduces the risk of electrical arcing caused by decontaminated items with metal components. The RF absorbing liner 125 can be formed from any suitable material selected to have a predetermined complex dielectric constant. The RF absorbing liner 125 has a thickness T that, together with the selected dielectric constant, results in desired RF absorptive properties. As an example, the RF absorbing liner 125 may have a thickness of about 1.5 inches (about 3.8 centimeters), although it may be more or less. The absorptive properties of the RF absorbing liner 125 enable the decontamination system 100 to achieve a substantially uniform cross-sectional power density across the selected frequency band of the RF energy output by the power amplifiers 115 and 116. Such a substantially uniform incident power density on a contaminated item may help to achieve a 100% effective deactivation, damage, or destruction of the contaminant.

Figure 5:
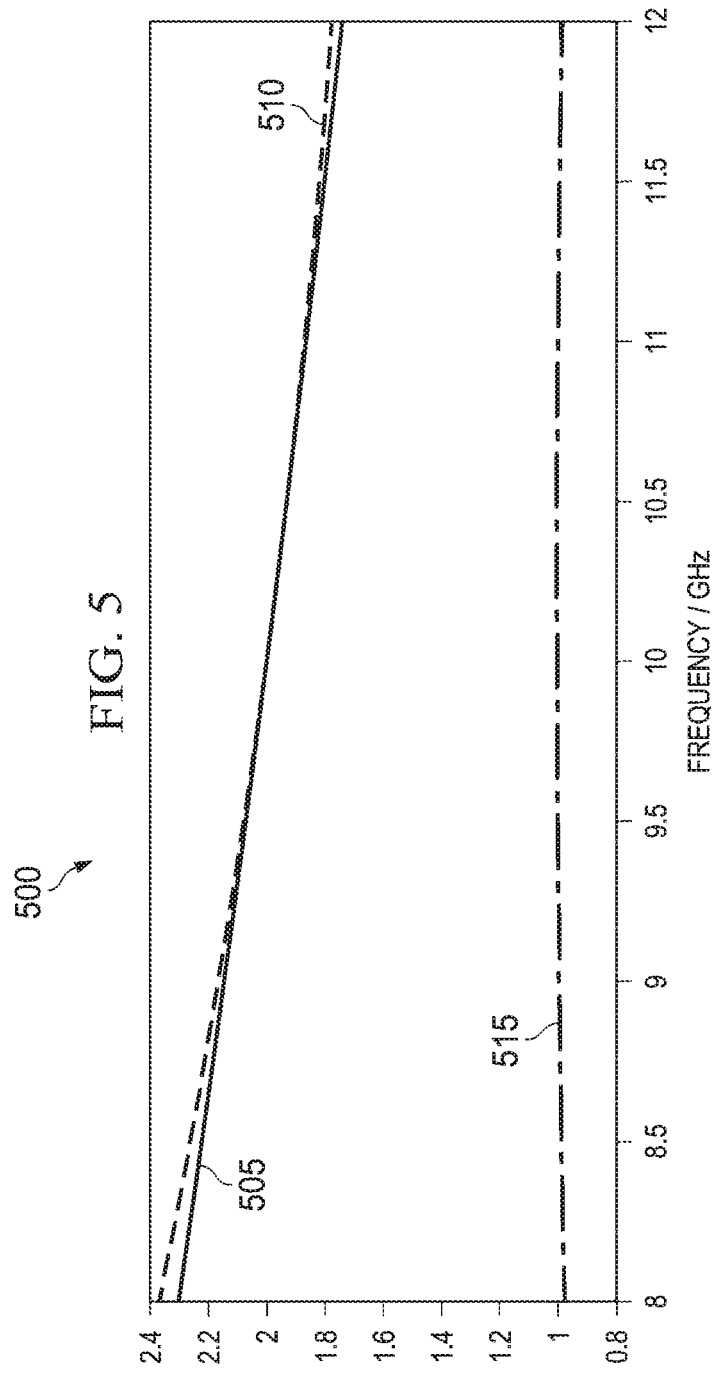
FIG. 5 illustrates a chart showing complex permittivity for an example embodiment of a radio frequency (RF) absorbing liner according to this disclosure.

The RF absorbing liner 125 exhibits a complex permittivity given by $\varepsilon=\varepsilon'-j\varepsilon''$, where $\varepsilon$ is the complex permittivity, $\varepsilon'$ is the real part of the permittivity, and $\varepsilon''$ is the imaginary part of the permittivity. The RF absorbing liner 125 can be selected to have a complex permittivity at the frequency of the RF energy that is advantageous for absorption of the RF energy. For example, FIG. 5 illustrates a chart 500 showing complex permittivity for an example embodiment of the RF absorbing liner 125 according to this disclosure. As shown in FIG. 5, a curve 505 indicates the real part of the permittivity $\varepsilon'$ for the RF absorbing liner 125 over a frequency range, and a curve 510 indicates the complex permittivity $\varepsilon''$ for the RF absorbing liner 125 over the frequency range. A curve 515 indicates the loss tangent $\varepsilon''/\varepsilon'$ for the RF absorbing liner 125 over the frequency range. For example, at a frequency of 10 GHz, the relative dielectric constant is approximately 2.0, the permittivity $\varepsilon=\varepsilon'-j\varepsilon''=2-j2$, and the loss tangent$=\varepsilon''/\varepsilon'=2/2=1$. Of course, the values shown in the chart 500 are mere examples, and other RF absorbing liners 125 having other permittivity values are possible and within the scope of this disclosure.

As discussed above, the decontamination system 100 produces a suitable (and possibly minimal) RF power density within the correct frequency band and with a substantially uniform power density across an entire contaminated item to effectively and efficiently deactivate, damage, or destroy 100% of a contaminant. In contrast, conventional systems that simply propagate RF energy across a contaminated item in a metal container are not 100% effective, since such systems suffer from high reflections that cause "high" and "low" power density regions, resulting in uneven power densities across a contaminated item that may not destroy all of the contaminant, or may excessively elevate the temperature of the contaminated item.

Figure 6:
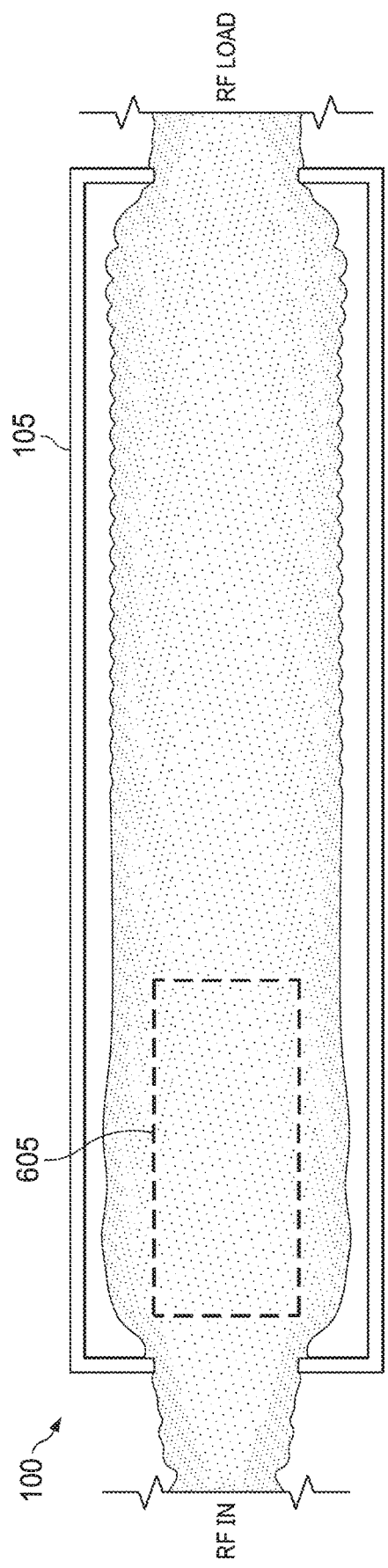
FIGS. 6 and 7 illustrate examples of power density levels exhibited during operation of the decontamination system of FIGS. 1 through 4 according to this disclosure.
Figure 7:
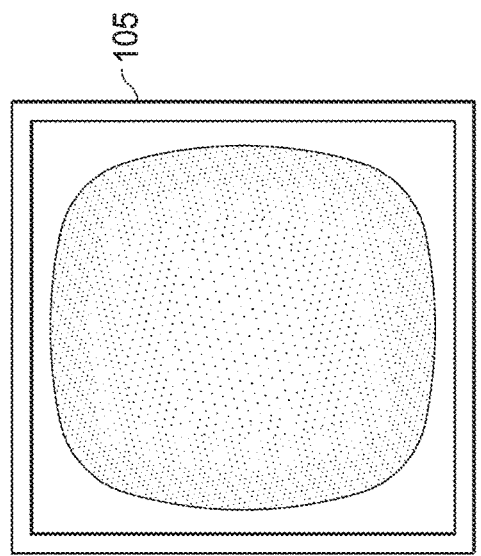

FIGS. 6 and 7 illustrate examples of power density levels exhibited during operation of the decontamination system 100 of FIGS. 1 through 4 according to this disclosure. In particular, FIG. 6 illustrates power density levels in a side view of the decontamination system 100, and FIG. 7 illustrates power density levels in a cross-sectional view of the decontamination system 100. As shown in FIGS. 6 and 7, different shadings reflect different levels of power density when only one power amplifier 115 operates. That is, the RF energy from the power amplifier 115 is input at one end of the decontamination system 100, while the other end of the decontamination system 100 is configured as an RF load. The uniformity of the different shadings and the smooth transitions between the different shadings indicate that the decontamination system 100 produces a substantially uniform cross-sectional power density of the RF energy. As used herein, a substantially uniform cross-sectional power density indicates that the level of incident RF energy across the cross section is substantially uniform and does not vary significantly between two adjacent locations. That is, the decontamination system 100 does not exhibit the randomly distributed areas of high and low power density, which are commonly found in conventional systems. In particular, a substantially uniform cross-sectional power density ensures that all spaces within the container 105 receive adequate energy to deactivate, damage, or destroy a contaminant without causing damage to the contaminated item(s).

A region 605 disposed toward one end of the container 105 represents a region where the RF power density is at a minimum threshold value to effectively decontaminate items. Prior to the decontamination operation, items to be decontaminated (such as PPE) can be placed in the region 605. The size of the region 605 can be based on various factors, such as the selected input power and the selected minimum threshold value for decontamination. In some embodiments, the length of the container 105 may be shortened to reduce the portion of the container 105 outside of the region 605, and the decontamination system 100 can still perform effectively. In embodiments with other selected values for the input power and the minimum threshold value, the region 605 may encompass more or less of the cavity 130 within the container 105.

The decontamination system 100 is adaptable to operate in a wide frequency range. For example, in some embodiments, the power amplifiers 115 and 116 can output RF energy in a range from about 8 GHz to about 12 GHz. It has been determined that the resonant frequency of the H3N2 virus is approximately 8.4 GHz. Therefore, to destroy the H3N2 virus on contaminated items, the decontamination system 100 can be configured to operate at approximately 8.4 GHz. A low amount of RF power density may be needed to destroy H3N2 at 8.4 GHz, and the decontamination system 100 can achieve this with only a 25 watt power amplifier 115 connected to the input of the horn 110. Of course, the decontamination system 100 can be tuned to other frequencies for decontamination of other viruses or contaminants having other resonant frequencies.

In some embodiments, the decontamination system 100 is configured for multiple modes of decontamination operation. In a "one-pass" mode, a single load containing one or more contaminated items (such as PPE) is placed into the container 105 toward one end, such as in the region 605 shown in FIG. 6. The power amplifier 115 excites the horn 110 with RF energy for a predetermined decontamination time period. The horn 110 propagates the RF energy along the length of the container 105 and through the contaminated item(s) to destroy the contaminant by molecular resonance. During this time period, the horn 111 is terminated so that the horn 111 provides an RF load to reduce reflected RF energy. Thus, some of the thru-power that is output from the power amplifier 115 is absorbed by the RF load in the horn 111, and additional power output is absorbed by the RF absorbing liner 125. Additionally or alternatively, the horn 111 can be connected to a sensor device (e.g., a power meter) to monitor the RF energy reaching the horn 111 while also reducing reflected energy. Such energy monitoring can be helpful to ensure that a suitable level of energy reaches the contaminated items.

In a "two-pass" sequential mode, the two horns 110 and 111 are powered in sequential passes. A single load containing one or more contaminated items is placed into the container 105 toward one end. In the first pass, the power amplifier 115 excites the horn 110 with RF energy for a first predetermined time period. During this time period, the horn 111 is terminated so that the horn 111 provides an RF load to absorb some of the thru-power and reduce reflected RF energy. In the second pass, the power amplifier 116 excites the horn 111 with RF energy for a second predetermined time period. During this time period, the horn 110 is terminated so that the horn 110 provides an RF load to absorb some of the thru-power and reduce reflected RF energy.

In a "simultaneous" mode, two contaminated loads can be simultaneously decontaminated. One load containing one or more contaminated items (such as PPE) is placed into the container 105 toward one end, such as in the region 605. A second load is placed into the container 105 toward the other end. Both horns 110 and 111 are then simultaneously excited with RF energy for a predetermined decontamination time period.

The decontamination time periods described above can vary depending on the contaminant(s) and the item(s) to be decontaminated. For the CV-19 virus, the decontamination time period is estimated to be a few minutes or less at a power density of about 850 W/m$^2$. This is a much shorter time than some conventional sterilization techniques that require hours to complete.

The design of the decontamination system 100 is flexible and can be scaled to accommodate different types of contaminants and contaminated items. For example, the dimensions of the container 105, the dimensions of the horn(s) 110 and 111, and the power output(s) of the power amplifier(s) 115 and 116 can be optimized to deliver a minimum power density required to effectively destroy a particular contaminant. As a particular example, larger dimensions for the horns 110 and 111 result in a lower power density for a given input power. Similarly, the frequency band of the generated power can be tuned to destroy a given contaminant at its resonant frequency. Other properties, such as the dimensions and the complex dielectric constant of the RF absorbing liner 125, can also be tuned for a particular contaminant.

In some embodiments, a calibration process can be performed when the container 105 is empty to ensure correct operation of the decontamination system 100. The calibration process can be performed, for example, prior to a decontamination process. In one example calibration process, the power amplifier 115 is activated, and the power received at the opposite horn 111 is measured. Then, the power amplifier 115 is turned off, the power amplifier 116 is activated, and the power received at the opposite horn 110 is measured. If the two measurements are substantially equal, the decontamination system 100 is operating properly. If the two measurements are different, there may be an issue with the decontamination system 100 that requires further investigation.

Figure 8:
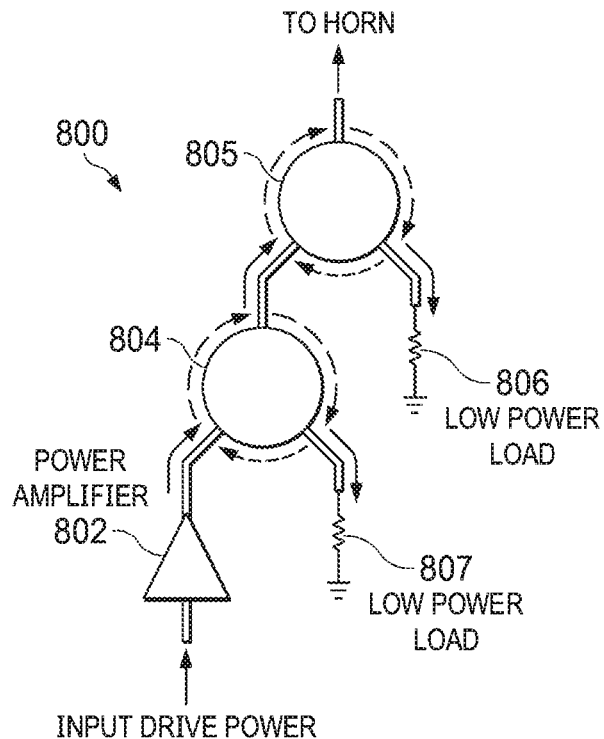
FIGS. 8 and 9 illustrate example power amplifier circuits that can be used in conjunction with the decontamination system of FIGS. 1 through 4 according to this disclosure.
Figure 9:
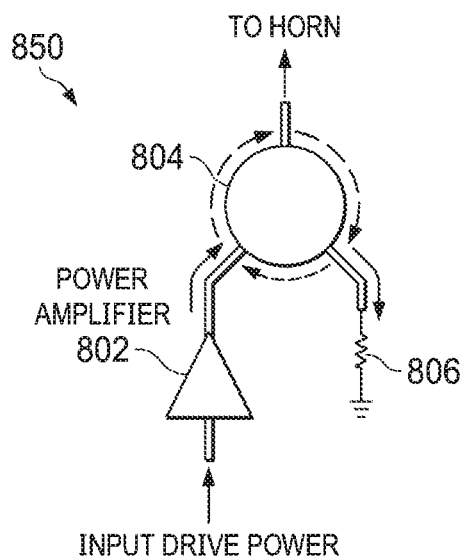

FIGS. 8 and 9 illustrate example power amplifier circuits that can be used in conjunction with the decontamination system 100 of FIGS. 1 through 4 according to this disclosure. In particular, FIG. 8 illustrates a power amplifier circuit 800 for simultaneous horn operation, and FIG. 9 illustrates a power amplifier circuit 850 for single horn operation. Each circuit 800, 850 is configured to provide a high level of isolation as discussed below.

As shown in FIG. 8, the circuit 800 is configured for simultaneous operation of two horns, one at each end of the decontamination system 100 (such as the horns 110 and 111). In this example embodiment, the decontamination system 100 includes two circuits 800, one for each horn 110 and 111. Each circuit 800 includes a power amplifier 802, which represents one of the power amplifiers 115 and 116. The power amplifier 802 is connected in series to two circulators 804 and 805, which isolate the power amplifier 802 in the circuit 800 in order to protect the power amplifier 802. The circulators 804 and 805 can be, for example, commercially available circulators. In some embodiments, each circulator 804 and 805 provides at least 20 dB isolation, and the total isolation to the power amplifier 802 is at least 40 dB. Each circulator 804 and 805 is connected to a corresponding low power load 806 and 807, respectively.

As shown in FIG. 9, the circuit 850 is configured for operation of one horn at a time. As in FIG. 8, the decontamination system 100 includes two circuits 850, one for each horn 110 and 111. The circuit 850 includes a power amplifier 802, which represents one of the power amplifiers 115 and 116. Here, the power amplifier 802 is connected to only one circulator 804, which isolates the power amplifier 802 in the circuit 800. In some embodiments, the circulator 804 provides at least about 20 dB isolation to the power amplifier 802. The circulator 804 is connected to a low power load 806.

Although FIGS. 1 through 9 illustrate one example of a decontamination system 100 and related details, various changes may be made to FIGS. 1 through 9. For example, the decontamination system 100 and its individual components may have any suitable sizes, shapes, and dimensions. Also, various components in the decontamination system 100 may be combined, further subdivided, replicated, rearranged, or omitted and additional components may be added according to particular needs. As a particular example, the decontamination system 100 may include a single horn 110 or 111 and a single power amplifier 115 or 116.

Figure 10:
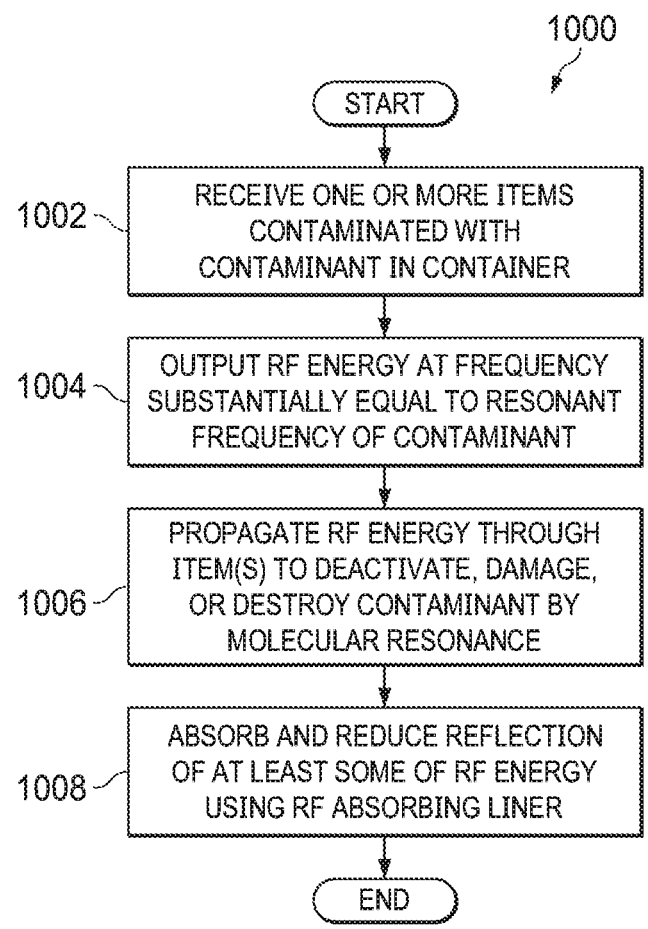
FIG. 10 illustrates an example method for decontamination of materials according to this disclosure.

FIG. 10 illustrates an example method 1000 for decontamination of materials according to this disclosure. For ease of explanation, the method 1000 is described as being performed using the decontamination system 100 of FIGS. 1 through 4. However, the method 1000 may be used with any other suitable device or system.

As shown in FIG. 10, one or more items that may be contaminated with a contaminant are received in a container at step 1002. This may include, for example, one or more contaminated items being placed in the cavity 130 of the container 105. In some embodiments, the one or more contaminated items include one or more pieces of PPE contaminated with the CV-19 virus.

RF energy is output by at least one power amplifier at a frequency substantially equal to a resonant frequency of the contaminant at step 1004. This may include, for example, at least one of the power amplifiers 115 and 116 outputting RF energy at approximately the resonant frequency of the contaminant. The RF energy is propagated along a length of the container to deactivate, damage, or destroy the contaminant by molecular resonance using at least one horn connected to the power amplifier(s) at step 1006. This may include, for example, at least one of the horns 110 and 111 propagating the RF energy along the length of the container 105. At least some of the RF energy is absorbed and reflection of at least some of the RF energy is reduced using an RF absorbing liner disposed on interior surfaces of the container at step 1008. This may include, for example, the RF absorbing liner 125 absorbing and reducing reflection of at least some of the RF energy in order to achieve a substantially uniform cross-sectional power density of the RF energy.

Although FIG. 10 illustrates one example of a method 1000 for decontamination of materials, various changes may be made to FIG. 10. For example, while shown as a series of steps, various steps shown in FIG. 10 may overlap, occur in parallel, occur in a different order, or occur multiple times. Also, some steps may be combined or removed and additional steps may be added according to particular needs.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in the present application should not be read as implying that any particular element, step, or function is an essential or critical element that must be included in the claim scope. The scope of patented subject matter is defined only by the allowed claims. Moreover, none of the claims is intended to invoke 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," or "system" within a claim is understood and intended to refer to structures known to those skilled in the relevant art, as further modified or enhanced by the features of the claims themselves, and is not intended to invoke 35 U.S.C. § 112(f).

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A system comprising:
  a container configured to hold one or more items contaminated with a contaminant;
  a power amplifier configured to output radio frequency (RF) energy at a frequency substantially equal to a resonant frequency of the contaminant;
  a horn connected to the power amplifier and configured to propagate the RF energy along a length of the container and through the one or more items to deactivate, damage, or destroy the contaminant by molecular resonance; and
  an RF absorbing liner disposed on interior surfaces of the container and configured to absorb and reduce reflection of at least some of the RF energy;
  wherein at least one of a thickness of the RF absorbing liner or a material of the RF absorbing liner is selected to achieve a substantially uniform cross-sectional power density of the RF energy.

2. The system of claim 1, wherein the horn is disposed at an end of the container.

3. The system of claim 1, wherein the power density is at least as large as a minimum power density required to deactivate, damage, or destroy the contaminant.

4. The system of claim 3, wherein at least one of dimensions of the container, dimensions of the horn, or an output power of the power amplifier is selected to enable the power density at which the RF energy is propagated through the container.

5. The system of claim 1, wherein the container comprises an outer layer formed of at least one metal, the at least one metal configured to reduce leakage of the RF energy outside the container.

6. The system of claim 1, further comprising:
  at least one circulator connected to the power amplifier, the at least one circulator configured to isolate the power amplifier.

7. The system of claim 1, wherein a cross section of the container is rectangular.

8. A system comprising:
  a container configured to hold one or more items contaminated with a contaminant;
  first and second power amplifiers each configured to output radio frequency (RF) energy at a frequency substantially equal to a resonant frequency of the contaminant;
  first and second horns each connected to one of the power amplifiers and configured to propagate the RF energy from that power amplifier along a length of the container and through the one or more items to deactivate, damage, or destroy the contaminant by molecular resonance; and
  an RF absorbing liner disposed on interior surfaces of the container and configured to absorb and reduce reflection of at least some of the RF energy;
  wherein at least one of a thickness of the RF absorbing liner or a material of the RF absorbing liner is selected to achieve a substantially uniform cross-sectional power density of the RF energy.

9. The system of claim 8, wherein the first and second horns are disposed at opposite ends of the container.

10. The system of claim 8, wherein the power density is at least as large as a minimum power density required to deactivate, damage, or destroy the contaminant.

11. The system of claim 10, wherein at least one of dimensions of the container, dimensions of the horns, or an output power of the power amplifiers is selected to enable the power density at which the RF energy is propagated through the container.

12. The system of claim 8, wherein the container comprises an outer layer formed of at least one metal, the at least one metal configured to reduce leakage of the RF energy outside the container.

13. The system of claim 8, further comprising:
  at least one circulator connected to each power amplifier, each circulator configured to isolate the power amplifier to which the circulator is connected.

14. The system of claim 8, wherein a cross section of the container is rectangular.

15. A method comprising:
  holding one or more items in a container, the one or more items contaminated with a contaminant;

outputting radio frequency (RF) energy by at least one power amplifier at a frequency substantially equal to a resonant frequency of the contaminant;

propagating the RF energy along a length of the container and through the one or more items to deactivate, damage, or destroy the contaminant by molecular resonance using at least one horn, wherein each of the at least one horn is connected to one of the at least one power amplifier; and absorbing and reducing reflection of at least some of the RF energy using an RF absorbing liner disposed on interior surfaces of the container;

wherein at least one of a thickness of the RF absorbing liner or a material of the RF absorbing liner is selected to achieve a substantially uniform cross-sectional power density of the RF energy.

16. The method of claim 15, wherein each of the at least one horn is disposed at an end of the container.

17. The method of claim 15, wherein the power density is at least as large as a minimum power density required to deactivate, damage, or destroy the contaminant.

18. The method of claim 17, wherein at least one of dimensions of the container, dimensions of the at least one horn, or at least one output power of the at least one power amplifier is selected to enable the power density at which the RF energy is propagated through the container.

19. The method of claim 15, further comprising:
reducing leakage of the RF energy outside the container using an outer layer of the container, the outer layer formed of at least one metal.

20. The method of claim 15, wherein a cross section of the container is rectangular.

* * * * *